(12) United States Patent
Hussein

US010517920B2

(10) Patent No.: US 10,517,920 B2
(45) Date of Patent: Dec. 31, 2019

(54) ANTIBACTERIAL PEPTIDE AND METHOD OF TREATMENT USING THE ANTIBACTERIAL PEPTIDE

(71) Applicant: United Arab Emirates University, Al Ain (AE)

(72) Inventor: Ahmed Soliman Hussein, Al Ain (AE)

(73) Assignee: United Arab Emirates University, Al Ain (AE)

( * ) Notice: Subject to any disclaimer, the term of this patent is extended or adjusted under 35 U.S.C. 154(b) by 117 days.

(21) Appl. No.: 15/595,313

(22) Filed: May 15, 2017

(65) Prior Publication Data
US 2017/0246240 A1    Aug. 31, 2017

Related U.S. Application Data

(60) Continuation-in-part of application No. 14/614,113, filed on Feb. 4, 2015, now Pat. No. 9,682,116, which is a division of application No. 13/284,173, filed on Oct. 28, 2011, now Pat. No. 8,968,729.

(51) Int. Cl.
| | |
|---|---|
| *A01N 37/18* | (2006.01) |
| *A61K 38/00* | (2006.01) |
| *A61P 31/00* | (2006.01) |
| *A61K 38/10* | (2006.01) |
| *A61K 38/08* | (2019.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 36/889* | (2006.01) |

(52) U.S. Cl.
CPC ............ *A61K 38/10* (2013.01); *A61K 36/889* (2013.01); *A61K 38/08* (2013.01)

(58) Field of Classification Search
None
See application file for complete search history.

(56) References Cited

U.S. PATENT DOCUMENTS

| | | | |
|---|---|---|---|
| 4,428,969 | A | 1/1984 | Muller et al. |
| 8,968,729 | B2 | 3/2015 | Hussein et al. |
| 9,682,116 | B2 | 6/2017 | Hussein et al. |
| 2017/0216389 | A1 | 8/2017 | Hussein et al. |

FOREIGN PATENT DOCUMENTS

| | | |
|---|---|---|
| CN | 1192329 A | 9/1998 |
| WO | 1996/037116 A1 | 11/1996 |

OTHER PUBLICATIONS

Saddiq AA and Bawazir AE "Antimicrobial Activity of Date Palm (*Phoenix dactylifera*) Pits Extracts and Its Role in Reducing the Side Effect of Methyl Prednisone on Some Neurotransmitter Content in the Brain, Hormone Testosterone in Adulthood" Proceedings of the 4th International Date Palm Conference. (Year: 2010).*

Belal I "Evaluating fungi-degraded date pits as a feed ingredient for Nile tilapia *Oreochromis niloticus* L." Aquaculture Nutrition 14: 445-452. (Year: 2008).*

Perveen et al. "Antibacterial activity of *Phoenix dactylifera* L. leaf and pit extracts against selected Gram negative and Gram positive pathogenic bacteria" J. Med. Plants Res. 6:296-300. (Year: 2012).*

Ziggers D "Date pits concept to be patented for anti bacterial properties" https://www.allaboutfeed.net/Nutrition/Feed-Additives/2011/4/Date-pits-concept-to-be-patented-for-anti-bacterial-properties-AAF005456W/ (Year: 2011).*

Kahkashan Perveen et al., "Antibacterial activity of *Phoenix dactylifera* L. leaf and pit extracts against selected Gram negative and Gram positive pathogenic bacteria," Journal of Medicinal Plants Research, vol. 6, No. 2, Jan. 16, 2012, 5 pgs.

Extended European Search Report dated Aug. 8, 2018, for corresponding European Application No. 18172352.9, 9 pgs.

Emmanuelle Landais, "Research Raises Hope for Drug-Free Chicken Meat." Gulf News, published Oct. 30, 2010, http://gulfnews.com/news/gulf/uae/environment/research-raises-hope-for-drug-free-chicken-meat-1.703781, 4 pages.

"Date Pits Tested as Antibiotic Replacement." The Poultry Site, published Apr. 7, 2011, http://www.thepoultrysite.com/poultrynews/22375/date-pits-tested-as-antibiotic-replacement, 3 pages.

Megan Detrie, "Researchers Test Date Pits as Replacement for Antibiotics." The National, published Apr. 7, 2011, http://www.thenational.ae/news/uae-news/science/researchers-test-date-pits-as-replacement-for-antibiotics, 2 pages.

"Date Pit as Poultry Antibiotic Concept to Be Patented in UAE." World Poultry, published Apr. 13, 2011, http://www.equimex.com/contact-us/linkedin/2003-date-pit-as-poultry-antibiotic-concept-to-be-patented-in-uae.html, 2 pages.

"Date Pits Concept to Be Patented for Anti Bacterial Properties." All About Feed, published Apr. 8, 2011, http://www.allaboutfeed.net/news/date-pits-concept-to-be-patented-for-anti-bacterial-properties-5456.html , 2 pages.

(Continued)

*Primary Examiner* — Christina Bradley
*Assistant Examiner* — Zachary J Miknis
(74) *Attorney, Agent, or Firm* — Fitch, Even, Tabin & Flannery LLP

(57) ABSTRACT

A method of treating or preventing a bacterial infection in an animal comprises administering to the animal an effective amount of an antibacterial peptide, the antibacterial peptide being derived from degraded date pits which are degraded by solid state degradation by a fungus, *Trichoderma reesei*. The antibacterial peptide has a molecular mass of less than 10 kDa and an amino acid sequence including (a) SEQ ID NO:4 or (b) SEQ ID NO:6. The bacterial infection is caused by a Gram-positive bacteria or a Gram-negative bacteria, for example, a *Salmonella* species, a *Campylobacter* species, a *Shigella* species, an *Escherichia* species, a *Pseudomonas* species, and a *Staphylococcus* species.

3 Claims, 10 Drawing Sheets

Specification includes a Sequence Listing.

(56) References Cited

OTHER PUBLICATIONS

Belal IEH. "Evaluation fungi-degraded date pits as a feed ingredient for Nile tilapia Oreochromis niloticus L." Aquaculture Nutrition, 2008, vol. 14, pp. 445-452.
Flemming JS. "Use of mannanoligosaccharides in broiler feeding." Brazilian Journal of Poultry Science. 2004, vol. 6, No. 3, pp. 159-161.
Hussein AS. "The use of dates and date pits in broiler starter and finisher diets." Bioresource Technology, 1998, vol. 66, pp. 219-223.
A. Aldhaheri, et al., "Chemical Composition of Date Pits and Reproductive Hormonal Status of Rats Fed Date Pits." Food Chemistry, vol. 86, 2004, pp. 93-97.
J.W. Bennet, et al., "Use of Fungi Biodegradation." Manual of Environmental Microbiology, Editor in Chief Christon J. Hurst, ASM Press Washington, D.C., 2002, pp. 960-971.
Souhail Besbes, et al., "Date Seeds: Chemical Composition and Characteristic Profiles of the Lipid Fraction." Food Chemistry, vol. 84, 2004, pp. 577-584.
Jonathan Gressel, et al., "Morphogenesis in Trichoderma: Photoinduction and RNA." Developmental Biology, vol. 15, 1967, pp. 575-598.
B.S. Kamel, et al. "Nutritional Value of Whole Dates and Date Pits in Broiler Rations." Poultry Science, vol. 60, 1981, pp. 1005-1011.
Seema Patel, et al., "Functional Oligosaccharides: Production, Properties and Applications." World Journal of Microbiology and Biotechnology, 2011, vol. 27, pp. 1119-1128.
J.M. Vandepopuliere, et al., "Dates and Date Pits as Ingredients in Broiler Starting and Coturnix Quail Breeder Diets." Poultry Science, vol. 74, 1995, pp. 1134-1142.
F. Vinale, et al., "Major Secondary Metabolites Produced by Two Commercial Trichoderma Strains Active Against Different Phytopathogens." Letters in Applied Microbiology, vol. 43, 2006, pp. 143-148.
Francesco Vinale, et al., "Trichoderma-Plant-Pathogen Interactions." Soil Biology & Biochemistry, vol. 40, 2008, pp. 1-10.
E. Bauza et al., "Date Palm Kernel Extract Exhibits Anti-aging Properties and Significantly Reduces Skin Wrinkles." International Journal of Tissue Reactions, vol. 24, No. 4, Jan. 1, 2002, pp. 131-136.
M. Khiyami et al., "Influence of Complex Nutrient Sources: Dates Syrup and Dates Pits on Lactococcus Lactis Growth and Nisin Production." Journal of Biotechnology, vol. 136S, Oct. 1, 2008, p. S736.
H. Najib et al., "Effect of Enzymatic Treatment of Saudi Date Pits on Performance of Single Comb White Leghorn Hens and the Fatty Acid Profile of Their Eggs." International Journal of Poultry Science, vol. 11, No. 10, 2012, pp. 624-629.
European Search Report, European Application No. 12190250.6, dated Mar. 25, 2013, 8 pages.
Oyofo et al., Prevention of *Salmonella typhimurium* colonization of broilers with D-mannose. Poult Sci. 1989, vol. 68, No. 10, pp. 1357-1360, abstract only.
Van Metre D., "Q fever." Colorado State University Extension, 2010, pp. 1-2.
MOS. Mannanase (beta-mannanase preparation). VTR. 2011; 1-4.
Biggs, P., et al., "The Effects of Several Oligosaccharides on Growth Performances, Nutrient Digestibilities, and Cecal Microbial Populations in Young Chicks." Poultry Science, 2007, vol. 86, No. 11, pp. 2327-2336, abstract only.
Chahal, D.S. "Solid-State Fermentation with Trichoderma reesei for Cellulase Production." Applied and Environmental Microbiology, Jan. 1985, vol. 49, No. 1, pp. 205-210, abstract only.
Chahal, Parminder S., et al., "Production of cellulase in solid-state fermentation with Trichoderma reesei MCG 80 on wheat straw." Applied Biochemistry and Biotechnology, 1996, vol. 57-58, issue 1, pp. 433-442, abstract only.
Kumprecht, I., et al., "Effects of Dietary Mannanoligosaccharide Level on Liveweight and Feed Efficiency of Broilers." Abstract No. S118, Supplement to vol. 76, Issue 1, Jan. 1997, Journal of Poultry Science, p. 132.
Latifian, Maryam, et al., "Evaluation of culture conditions for cellulase production by two Trichoderma reesei mutants under solid-state fermentation conditions." Bioresource Technology, vol. 98, issue 18, Dec. 2007, pp. 3634-3637, abstract only.
Novak, Curtis, et al., "Use of Bio-Mos® to Control *Salmonella* and Campylobacter in Organic Poultry." Department Animal and Poultry Sciences, Virginia Tech, Blacksburg, Virginia, <http://www.zootecnicainternational.com/article-archive/nutrition/563-use-of-biomosr-to-control-salmonella-and-campylobacter-in-organic-poultry-.html> Jul. 1, 2007, 5 pages.
Singhania, Reeta Rani, et al., "Solid-state fermentation of lignocellulosic substrates for cellulase production by Trichoderma reesei NRRL 11460." Indian Journal of Biotechnology, vol. 5, (Suppl), Jul. 2006, pp. 332-336.
FDA. FDA 101: dietary supplements. www.fda.gov.2008;1-3.

* cited by examiner

| Component | Non-degraded date pits (sub batch 1) (%) | Processed wet degraded date pits (sub batch 2) (%) | Processed solid state degraded date pits (sub batch 3) (%) |
|---|---|---|---|
| Total carbohydrate | 3.4 | 3.9 | 7.8 |
| Cellulose | 25.6 | 26.3 | 42.3 |
| Hemicellulose | 13.2 | 13.8 | 35.4 |
| Lignin | 8.3 | 8.5 | 15.2 |
| Soluble polysaccharide | 70.4 | 71.2 | 89.7 |
| Pectin | 0.9 | 0.8 | 8.9 |
| Mannan oligosaccharide | 17.3 | 18.2 | 30.7 |
| Crude fibre | 22.7 | 18.2 | 14.5 |
| Acid detergent fibre | 56.9 | 48.8 | 44.3 |
| Neutral Detergent fibre | 65.6 | 72.3 | 84.6 |

Figure 2

| Monosaccharide | Non-degraded date pits (sub batch 1) (%) | Processed wet degraded date pits (sub batch 2) (%) | Processed solid state degraded date pits (sub batch 3) (%) |
|---|---|---|---|
| Galactose | 22.8 | 23.6 | 33.5 |
| Glucose | 12.7 | 13.3 | 27.9 |
| Mannose | 7.2 | 8.1 | 23.5 |
| Arabinose | 2.4 | 3.2 | 6.9 |
| Rhamnose | 2.8 | 4.1 | 10.2 |
| Fructose | Not detected | Not detected | Not detected |
| Xylose | 0.53 | 0.72 | 5.8 |
| Galacturonic acid | 56.3 | 42.1 | 36.8 |
| Glucuronic acid | 2.2 | 2.8 | 6.1 |

Figure 3

| Monosaccharide | Non-degraded date pits (sub batch 1) (%) | Processed wet degraded date pits (sub batch 2) (%) | Processed solid state degraded date pits (sub batch 3) (%) |
|---|---|---|---|
| Fructose | 0.2 | 0.5 | 1.5 |
| Glucose | 22.4 | 25.6 | 41.3 |
| Mannose | 14.7 | 15.3 | 36.8 |
| Xylose | 7.4 | 8.5 | 10.8 |
| Galactose | 32.7 | 33.0 | 48.3 |
| Arabinose | 4.4 | 5.9 | 8.9 |
| Sucrose | 0.8 | 1.1 | 1.9 |
| Fucose | Not detected | Not detected | Not detected |

Figure 4

| Monosaccharides | Non-degraded date pits (sub batch 1) (%) | Processed wet degraded date pits (sub batch 2) (%) | Processed solid state degraded date pits (sub batch 3) (%) |
|---|---|---|---|
| Fructose | 5.7 | 6.2 | 8.2 |
| Glucose | 15.6 | 17.3 | 32.8 |
| Mannose | 9.8 | 10.6 | 33.2 |
| Xylose | 8.9 | 10.3 | 19.6 |
| Galactose | 23.6 | 26.3 | 47.8 |
| Arabinose | 2.8 | 5.5 | 7.6 |
| Sucrose | 2.7 | 8.3 | 9.2 |
| Fucose | Not detected | 0.21 | Not detected |

Figure 5

| Monosaccharide | Non-degraded date pits (sub batch 1) (%) | Processed wet degraded date pits (sub batch 2) (%) | Processed solid state degraded date pits (sub batch 3) (%) |
|---|---|---|---|
| Fructose | 0.2 | 0.5 | 1.43 |
| Glucose | 6.5 | 7.4 | 18.6 |
| Mannose | 0.53 | 0.74 | 5.2 |
| Xylose | 2.9 | 5.8 | 9.5 |
| Galactose | 2.3 | 3.6 | 6.9 |
| Arabinose | 0.8 | 2.7 | 2.4 |
| Sucrose | 0.5 | 0.8 | 0.8 |
| Fucose | Not detected | Not detected | Not detected |

Figure 6

| Monosaccharide | Non-degraded date pits (sub batch 1) (%) | Processed wet degraded date pits (sub batch 2) (%) | Processed solid state degraded date pits (sub batch 3) (%) |
|---|---|---|---|
| Fructose | Not detected | Not detected | Not detected |
| Glucose | 0.25 | 0.3 | 4.2 |
| Mannose | 0.73 | 0.81 | 6.3 |
| Xylose | 0.1 | 0.4 | 1.9 |
| Galactose | 0.8 | 1.7 | 5.3 |
| Arabinose | Not detected | 0.4 | 2.8 |
| Sucrose | Not detected | Not detected | Not detected |
| Fucose | Not detected | Not detected | Not detected |

Figure 7

| Monosaccharide | Non-degraded date pits (sub batch 1) (%) | Processed wet degraded date pits (sub batch 2) (%) | Processed solid state degraded date pits (sub batch 3) (%) |
|---|---|---|---|
| Fructose | 5.1 | 7.4 | 12.5 |
| Galactose | 28.2 | 31.5 | 54.5 |
| Mannose | 39.6 | 41.6 | 70.7 |
| Glucose | 22.8 | 26.5 | 42.6 |
| Arabinose | 5.2 | 7.9 | 15.2 |
| Xylose | 4.9 | 5.8 | 19.5 |
| Sucrose | 4.3 | 6.9 | 13.8 |
| Fucose | Not detected | Not detected | Not detected |

Figure 8

| Name of the bacteria | Control (Un-degraded date pits) (sub batch 1) (inhibition zone in mm) | Degraded date pits (Wet degradation method) (sub batch 2) (inhibition zone in mm) | Degraded date pits (Solid state degradation method) (sub batch 3) (inhibition zone in mm) |
|---|---|---|---|
| *Staphylococcus aureus* | 0 a | 0 a | 28 b |
| *Pseudomonas aeruginosa* | 0 a | 0 a | 21 b |
| *Salmonella typhimurium* | 0 a | 0 a | 25 b |
| *Escherichia coli* | 0 a | 0 a | 22 b |

Figure 9

| Bacterial species | Zone of Inhibition (mm) Fractionated Peptides from sample 1 (1000μg/ml) | | | | Phosphate Buffer | Ampicillin standard |
|---|---|---|---|---|---|---|
| | <10 kDa | 10-30 kDa | 30-50 kDa | > 50 kDa | 10μL | 10 μg/mL |
| E.Coli | 0±0.00 | 0±0.00 | 0±0.00 | 0±0.00 | 0±0.00 | 27.1±1.38 |
| S.typhimurium | 0±0.00 | 0±0.00 | 0±0.00 | 0±0.00 | 0±0.00 | 30.5±1.47 |
| S.aureus | 0±0.00 | 0±0.00 | 0±0.00 | 0±0.00 | 0±0.00 | 24.6±1.19 |
| B.subtilis | 0±0.00 | 0±0.00 | 0±0.00 | 0±0.00 | 0±0.00 | 25.5±1.23 |
| P.Vulgaris | 0±0.00 | 0±0.00 | 0±0.00 | 0±0.00 | 0±0.00 | 27.2±1.31 |

Figure 14

| Bacterial species | Sample 2 Zone of Inhibition (mm) Fractionated Peptides (1000μg/ml) | | | | Sample 3 Zone of Inhibition (mm) Fractionated Peptides (1000μg/ml) | | | | Phosphate Buffer | Ampicillin Standard |
|---|---|---|---|---|---|---|---|---|---|---|
| | <10 kDa | 10-30 kDa | 30-50 kDa | > 50 kDa | <10 kDa | 10-30 kDa | 30-50 kDa | > 50 kDa | 10μL | 10 μg/mL |
| E.Coli | 0±0.00 | 0±0.00 | 0±0.00 | 0±0.00 | 19.58±0.29 | 10.23±0.30 | 8.87±0.11 | 7.56±0.21 | 0 | 27.1±1.38 |
| S.typhimurium | 0±0.00 | 0±0.00 | 0±0.00 | 0±0.00 | 21.1±0.35 | 13.56±0.09 | 4.13±0.45 | 3.20±0.00 | 0 | 30.5±1.47 |
| S.aureus | 0±0.00 | 0±0.00 | 0±0.00 | 0±0.00 | 13.0±0.13 | 8.47±0.45 | 7.85±0.00 | 0±0.00 | 0 | 24.6±1.19 |
| B.subtilis | 0±0.00 | 0±0.00 | 0±0.00 | 4.67±0.21 | 7.69±0.20 | 3.87±0.50 | 0±0.00 | 0±0.00 | 0 | 25.5±1.23 |
| P.Vulgaris | 0±0.00 | 0±0.00 | 0±0.00 | 0±0.00 | 0±0.00 | 0±0.00 | 0±0.00 | 0±0.00 | 0 | 27.2±1.31 |

Figure 15

| SEQ ID NO: | Peptide Sequence | Molecular mass (Da) | Activity |
|---|---|---|---|
| 7 | AAVALLPAVLLALLAPAAANYKKPKL | 556.53 | - |
| 8 | LIRLWSHLIHIWFQNRRLKWKKK | 336.21 | - |
| 9 | DVISTHPLPVDVISTHPLPVIKEL | 766.75 | - |
| 10 | SYDTKFEEINKVLFG | 445.19 | - |
| 11 | ETWNPNNKPFQ | 896.43 | - |
| 12 | ALKPDNRIESEGGLIETWNPNNKPFQCAGVALSRCT | 673.27 | - |
| 13 | LLREQYEEEQEAKAELQRGMSKA | 465.52 | - |
| 14 | YETDAIQRTEELEEAKKK | 645.19 | - |
| 15 | AAVPSGASTGVHEALEL | 596.23 | - |
| 16 | NRRIQLVEEELDRAQER | 773.17 | - |
| 17 | Trp-Ala-Ala-Phe-Pro-Pro-Phe-Asp-Val-Ala-Gly-Asn-Val-Asp-Tyr-Lys-Asn | 965.52 | Anti-bacterial |
| 18 | AEQELVDASERVGL | 325.23 | - |

Figure 16

| SEQ ID NO: | Peptide Sequence | Molecular mass (Da) | Activity |
|---|---|---|---|
| 1 | Leu-Glu-Gly-Asp-Leu-Lys-Leu-Ser-Gln-Glu | 504.3279 | |
| 2 | Gln-Glu-Leu-Leu-Asn-Pro-Thr-His-Gln-Ile-Tyr-Pro-Val-Thr-Leu- | 817.2387 | |
| 3 | His-His-Pro-Asp-Asp-Phe-Asn-Pro-Ser-Val-His | 845.2901 | |
| 4 | Lys-Arg-Gly-Arg-Leu-Ile-Trp-Arg-Val-Trp-Arg-Gly-Ile-Trp | 732.2129 | Antibacterial |
| 5 | Glu-Arg-Ala-lys-Tyr-Pro-Leu-Pro-His | 374.2348 | |
| 6 | Arg-Gln-Trp-Ile-Ser-Arg-Trp-Thr-Trp-Gln-Arg | 482.6345 | Antibacterial |

Figure 17

| Bacterial species | Sample 2 Zone of Inhibition(mm) | | Sample 3 Zone of Inhibition(mm) | | | | Phosphate Buffer control (10μL) | Ampicillin Standard (10μg/mL) |
|---|---|---|---|---|---|---|---|---|
| | SEQ ID NO:17 | | SEQ ID NO:4 | | SEQ ID NO:6 | | | |
| | 500 μg/mL | 1000 μg/mL | 500 μg/mL | 1000 μg/mL | 500 μg/mL | 1000 μg/mL | | |
| E.Coli | 0±0.00 | 0±0.00 | 10.23±0.20 | 19.13±0.12 | 12.23±0.11 | 22.13±0.45 | 0±0.00 | 27.1±1.38 |
| S.typhimurium | 0±0.00 | 0±0.00 | 8.16±0.00 | 13.45±0.09 | 15.61±0.66 | 25.04±0.68 | 0±0.00 | 30.5±1.47 |
| S.aureus | 0±0.00 | 0±0.00 | 11.4±0.38 | 17.21±0.40 | 11.55±0.15 | 20.23±0.69 | 0±0.00 | 24.6±1.19 |
| B.subtilis | 0±0.00 | 8.23.±0.12 | 6.2±0.50 | 15.11±0.59 | 14.52±0.43 | 19.25±0.52 | 0±0.00 | 25.5±1.23 |
| P.Vulgaris | 0±0.00 | 0±0.00 | 4.12±0.30 | 9.12±0.20 | 0±0.00 | 5.23±0.90 | 0±0.00 | 27.2±1.31 |

Figure 18

SEQUENCE LISTING

<160> NUMBER OF SEQ ID NOS: 18

<210> SEQ ID NO 1

-continued

```
<211> LENGTH: 10
<212> TYPE: PRT
<213> ORGANISM: Artificial Sequence
<220> FEATURE:
<223> OTHER INFORMATION: Peptide obtained from date pits degraded by
      solid state degradation

<400> SEQUENCE: 1

Leu Glu Gly Asp Leu Lys Leu Ser Gln Glu
1               5                   10

<210> SEQ ID NO 2
<211> LENGTH: 15
<212> TYPE: PRT
<213> ORGANISM: Artificial Sequence
<220> FEATURE:
<223> OTHER INFORMATION: Peptide obtained from date pits degraded by
      solid state degradation

<400> SEQUENCE: 2

Gln Glu Leu Leu Asn Pro Thr His Gln Ile Tyr Pro Val Thr Leu
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Peptide obtained from date pits degraded by
      solid state degradation

<400> SEQUENCE: 3

His His Pro Asp Asp Phe Asn Pro Ser Val His
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide obtained from date pits degraded by
      solid state degradation

<400> SEQUENCE: 4

Lys Arg Gly Arg Leu Ile Trp Arg Val Trp Arg Gly Ile Trp
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Peptide obtained from date pits degraded by
      solid state degradation

<400> SEQUENCE: 5

Glu Arg Ala Lys Tyr Pro Leu Pro His
1               5

<210> SEQ ID NO 6
<211> LENGTH: 11
<212> TYPE: PRT
<213> ORGANISM: Artificial Sequence
<220> FEATURE:
<223> OTHER INFORMATION: Peptide obtained from date pits degraded by
      solid state degradation

<400> SEQUENCE: 6
```

```
Arg Gln Trp Ile Ser Arg Trp Thr Trp Gln Arg
1               5                  10

<210> SEQ ID NO 7
<211> LENGTH: 26
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 7

Ala Ala Val Ala Leu Leu Pro Ala Val Leu Leu Ala Leu Leu Ala Pro
1               5                  10                  15

Ala Ala Ala Asn Tyr Lys Lys Pro Lys Leu
            20                  25

<210> SEQ ID NO 8
<211> LENGTH: 23
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 8

Leu Ile Arg Leu Trp Ser His Leu Ile His Ile Trp Phe Gln Asn Arg
1               5                  10                  15

Arg Leu Lys Trp Lys Lys Lys
            20

<210> SEQ ID NO 9
<211> LENGTH: 26
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 9

Asp Val Ile Ser Thr Ile Ile Pro Leu Pro Val Asp Val Ile Ser Thr
1               5                  10                  15

Ile Ile Pro Leu Pro Val Ile Lys Glu Leu
            20                  25

<210> SEQ ID NO 10
<211> LENGTH: 15
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 10

Ser Tyr Asp Thr Lys Phe Glu Glu Ile Asn Lys Val Leu Phe Gly
1               5                  10                  15

<210> SEQ ID NO 11
<211> LENGTH: 11
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 11
```

```
Glu Thr Trp Asn Pro Asn Asn Lys Pro Phe Gln
1               5                   10
```

<210> SEQ ID NO 12
<211> LENGTH: 36
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 12

```
Ala Leu Lys Pro Asp Asn Arg Ile Glu Ser Glu Gly Gly Leu Ile Glu
1               5                   10                  15

Thr Trp Asn Pro Asn Asn Lys Pro Phe Gln Cys Ala Gly Val Ala Leu
            20                  25                  30

Ser Arg Cys Thr
            35
```

<210> SEQ ID NO 13
<211> LENGTH: 23
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 13

```
Leu Leu Arg Glu Gln Tyr Glu Glu Gln Glu Ala Lys Ala Glu Leu
1               5                   10                  15

Gln Arg Gly Met Ser Lys Ala
            20
```

<210> SEQ ID NO 14
<211> LENGTH: 18
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 14

```
Tyr Glu Thr Asp Ala Ile Gln Arg Thr Glu Glu Leu Glu Glu Ala Lys
1               5                   10                  15

Lys Lys
```

<210> SEQ ID NO 15
<211> LENGTH: 17
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 15

```
Ala Ala Val Pro Ser Gly Ala Ser Thr Gly Val His Glu Ala Leu Glu
1               5                   10                  15

Leu
```

<210> SEQ ID NO 16
<211> LENGTH: 17
<212> TYPE: PRT
<213> ORGANISM: Artificial Sequence
<220> FEATURE:
<223> OTHER INFORMATION: Peptide obtained from date pits degraded by wet

```
                        degradation

<400> SEQUENCE: 16

Asn Arg Arg Ile Gln Leu Val Glu Glu Glu Leu Asp Arg Ala Gln Glu
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 17

Trp Ala Ala Phe Pro Pro Phe Asp Val Ala Gly Asn Val Asp Tyr Lys
1               5                   10                  15

Asn

<210> SEQ ID NO 18
<211> LENGTH: 14
<212> TYPE: PRT
<213> ORGANISM: Artificial Sequence
<220> FEATURE:
<223> OTHER INFORMATION: Peptide obtained from date pits degraded by wet
      degradation

<400> SEQUENCE: 18

Ala Glu Gln Glu Leu Val Asp Ala Ser Glu Arg Val Gly Leu
1               5                   10
```

ANTIBACTERIAL PEPTIDE AND METHOD OF TREATMENT USING THE ANTIBACTERIAL PEPTIDE

CROSS REFERENCE TO RELATED APPLICATIONS

This application is a continuation in part application of U.S. application Ser. No. 14/614,113 filed on Feb. 4, 2015, which is a divisional application of U.S. application Ser. No. 13/284,173 filed Oct. 28, 2011, now U.S. Pat. No. 8,968,729, issued on Mar. 3, 2015. The contents of both U.S. application Ser. No. 14/614,113 and Ser. No. 13/284,173 are incorporated herein by reference in their entirety.

SEQUENCE LISTING

The instant application contains a sequence listing which was submitted herewith. The sequence listing file in ASCII text format, is named Sequence_Listing_140973_ST25.txt, is 5.74 KB in size, was created on May 15, 2017, and is incorporated herein by reference in its entirety.

FIELD OF THE INVENTION

This invention relates to an antibacterial peptide and compositions including the peptide for treating and preventing bacterial infections in an animal. The invention relates more particularly to an antibacterial peptide derived from degraded date pits. The invention relates further to a method of treatment using the antibacterial peptide.

BACKGROUND OF THE INVENTION

Sub-therapeutic doses of antibiotics have routinely been administered to animals in order to promote weight gain in apparently healthy animals. While supplementing animal feed with antibiotics can have a number of benefits, concerns exist over the use of conventional antibiotics in animal feed and water. The use of antibiotics in sub-therapeutic levels in animals has been implicated in the rise in antibiotic resistance of bacteria. Additionally, residual antibiotics may remain in meat products that are meant for human consumption.

To address these concerns the US Food and Drug agency (FDA) require that that antibiotic must be withdrawn from the feed of the animal at least two weeks prior to slaughter to prevent antibiotics remaining in the animal that is to enter the human food chain. The European Union and other countries require that antibiotics are not used as growth promoters in animal feed. Furthermore feed composition costs make a large proportion of the costs in animal production.

Date pits are readily available in a number of countries. Date pits have typically been seen as waste product from the preparation of dates and are usually discarded.

SUMMARY OF THE INVENTION

An object of the invention is to provide methods and compositions to treat and prevent bacterial infections in domestic animals.

A further object of the invention is to provide an alternative to conventional antibiotics to treat and prevent bacterial infections in domestic animals.

A further object of the invention is to provide a growth promoter for promoting growth in an animal.

In one aspect, the invention comprises a method of treating an animal comprising: administering to the animal an effective amount of an antibacterial peptide, the antibacterial peptide being derived from degraded date pits which are degraded by solid state degradation. More particularly, the method of treating the animal may be a method of promoting growth in the animal. The method of treating the animal may be a method of preventing bacterial infections in the animal. The method of treating the animal may be a method of treating bacterial infections in the animal.

The antibacterial peptide may have a molecular mass selected from the group consisting of: more than 50 kDa, from 30 to 50 kDa, from 10 to 30 kDa, and less than 10 kDa. Preferably, the antibacterial peptide may have a molecular mass of less than 10 kDa.

The antibacterial peptide may have less than 15 amino acids in its sequence. The degraded date pits may be fungi degraded date pits. The degraded date pits may be in the form of *Trichoderma reesei* degraded date pits.

The antibacterial peptide may have an amino acid sequence including an amino acid sequence selected from the group consisting of:
(a) SEQ ID NO:4 and functional derivatives thereof; and
(b) SEQ ID NO:6 and functional derivatives thereof.

The method may include administering the antibacterial peptide in an effective amount thereby preventing or delaying the onset of a bacterial infection in the animal, or reducing the microbial load in the animal or inhibiting the growth or killing bacterium in the animal. The method may allow a reduction in the amount of conventional antibiotics that will need to be administered to the animal to maintain animal health.

The bacterial infection may be caused by one of a Gram-positive bacteria and Gram-negative bacteria. More specifically, the bacterial infection may be caused by one of a *Salmonella* species, a *Campylobacter* species, a *Shigella* species, an *Escherichia* species, a *Pseudomonas* species, and a *Staphylococcus* species.

The method may be used for treating an animal selected from the group consisting of cattle, horses, pigs, goats, fish and poultry. Preferably the animal is poultry.

A further aspect of the invention comprises a method treating an animal comprising: administering to the animal an effective amount of an antibacterial peptide having an amino acid sequence including an amino acid sequence selected from the group consisting of:
(a) SEQ ID NO:4 and functional derivatives thereof; and
(b) SEQ ID NO:6 and functional derivatives thereof.

The method of treating the animal may be a method of promoting growth in the animal. The method of treating the animal may be a method of treating bacterial infection in the animal. The method of treating the animal may be a method of preventing bacterial infection in the animal. The method of treating the animal may be a method of preventing or delaying the onset of a bacterial infection in the animal, or reducing the microbial load in the animal or inhibiting the growth or killing bacterium in the animal. The method may allow a reduction in the amount of conventional antibiotics that will need to be administered to the animal to maintain animal health.

In another aspect, the invention comprises an antibacterial peptide derived from degraded date pits which are degraded by solid state degradation.

The antibacterial peptide may have a molecular mass selected from the group consisting of: more than 50 kDa, between 30 to 50 kDa, between 10 to 30 kDa and less than 10 kDa. Preferably, the antibacterial peptide may have a molecular mass of less than 10 kDa.

The antibacterial peptide may have less than 15 amino acids in its sequence. The degraded date pits may be fungi treated date pits. The degraded date pits may be in the form of *Trichoderma reesei* degraded date pits.

The antibacterial peptide may have an amino acid sequence including an amino acid sequence selected from the group consisting of:
(a) SEQ ID NO:4 and functional derivatives thereof; and
(b) SEQ ID NO:6 and functional derivatives thereof.

In yet another aspect, the invention comprises an antibacterial peptide for use in a method of treating an animal, the antibacterial peptide being derived from degraded date pits which are degraded by solid state degradation.

The antibacterial peptide may have a molecular mass selected from the group consisting of: more than 50 kDa, between 30 to 50 kDa, between 10 to 30 kDa and less than 10 kDa. Preferably, the antibacterial peptide may have a molecular mass of less than 10 kDa.

The antibacterial peptide may have less than 15 amino acids in its sequence. The degraded date pits may be fungi treated date pits. The degraded date pits may be in the form of *Trichoderma reesei* degraded date pits.

The antibacterial peptide may have an amino acid sequence including an amino acid sequence selected from the group consisting of:
(a) SEQ ID NO:4 and functional derivatives thereof; and
(b) SEQ ID NO:6 and functional derivatives thereof.

The method may be for preventing or delaying the onset of a bacterial infection in the animal, or reducing the microbial load in the animal or inhibiting the growth or killing bacterium in the animal. The method may allow a reduction in the amount of conventional antibiotics that will need to be administered to the animal to maintain animal health. The method may be a method of promoting growth in an animal. The method may be a method of preventing bacterial infections in the animal. The method may be a method of treating bacterial infections in the animal.

In yet another aspect, the invention comprises an isolated nucleic acid molecule/recombinant/synthetic amino acid sequence including an amino acid sequence selected from the group consisting of:
(a) SEQ ID NO:4 and functional derivatives thereof; and
(b) SEQ ID NO:6 and functional derivatives thereof.

In still another aspect, the invention comprises the use of an antibacterial peptide in the manufacture of a composition for treating an animal, the antibacterial peptide being an antibacterial peptide as defined and described hereinabove. The antibacterial peptide may be derived from date pits degraded by solid state degradation.

The antibacterial peptide may have a molecular mass selected from the group consisting of: more than 50 kDa, between 30 to 50 kDa, between 10 to 30 kDa and less than 10 kDa. Preferably, the antibacterial peptide may have a molecular mass of less than 10 kDa.

The antibacterial peptide may have less than 15 amino acids in its sequence. The degraded date pits may be fungi treated date pits. The degraded date pits may be in the form of *Trichoderma reesei* degraded date pits.

The antibacterial peptide may have an amino acid sequence including an amino acid sequence selected from the group consisting of:
(a) SEQ ID NO:4 and functional derivatives thereof; and
(b) SEQ ID NO:6 and functional derivatives thereof.

The composition may be for use in an effective amount thereby preventing or delaying the onset of a bacterial infection in the animal, or reducing the microbial load in the animal or inhibiting the growth or killing bacterium in the animal. The composition may be for allowing a reduction in the amount of conventional antibiotics that will need to be administered to the animal to maintain animal health. The composition may be in the form of a feed composition.

The bacterial infection may be caused by one of a Gram-positive bacteria and Gram-negative bacteria. More specifically, the bacterial infection may be caused by one of a *Salmonella* species, a *Campylobacter* species, a *Shigella* species, an *Escherichia* species, a *Pseudomonas* species, and a *Staphylococcus* species.

The composition may be for treating an animal selected from the group consisting of cattle, horses, pigs, goats, fish and poultry. Preferably the animal is poultry.

The composition may be for promoting growth in the animal. The composition may be for preventing bacterial infections in the animal. The composition may be for treating bacterial infections in the animal.

BRIEF DESCRIPTION OF THE DRAWINGS

FIG. 2 shows a table showing the chemical composition of wet degraded date pits, solid state degraded date pits and non-degraded date pit;

FIG. 3 shows a table showing monosaccharide composition of mannan oligosaccharide in wet degraded date pits, solid state degraded date pits and non-degraded date pit;

FIG. 4 shows a table showing monosaccharide composition of Cellulose in wet degraded date pits, solid state degraded date pits and non-degraded date pit;

FIG. 5 shows a table showing monosaccharide composition of Hemicellulose in wet degraded date pits, solid state degraded date pits and non-degraded date pit;

FIG. 6 shown a table showing monosaccharide composition of Lignin in wet degraded date pits, solid state degraded date pits and non-degraded date pit;

FIG. 7 shows a table showing monosaccharide composition of pectin in wet degraded date pits, solid state degraded date pits and non-degraded date pit;

FIG. 8 shows a table showing monosaccharide composition of soluble polysaccharides in wet degraded date pits, solid state degraded date pits and non-degraded date pit;

FIG. 9 shows a table showing antibacterial effect of wet degraded date pits, solid state degraded date pits and non-degraded date pit;

FIG. 14 shows a table showing anti-bacterial activity of peptide fractions from non-degraded date pits (sample 1);

FIG. 15 shows a table showing anti-bacterial activity of <10 kDa, 10-30 kDa, 30-50 kDa and >50 kDa peptide fractions from date pits degraded by wet degradation (sample 2) and date pits degraded by solid state degradation (sample 3);

FIG. 16 shows a table showing the peptide sequences present in date pits degraded by wet degradation;

FIG. 17 shows a table showing several peptide sequences present in date pits degraded by solid state degradation; and FIG. 18 shows a table showing the antibacterial activity of identified antibacterial sequences (SEQ ID NO:4 and SEQ ID NO:6) from the peptide sequences shown in FIG. 17.

DETAILED DESCRIPTION OF THE INVENTION

The invention comprises methods and compositions for treating and preventing bacterial infections in animals. The composition comprises degraded date pits which are administered to animals in an effective amount to treat or prevent bacterial infection. This invention relates also to an antibacterial peptide for treating and preventing bacterial infections in an animal. More specifically, the invention relates also to an antibacterial peptide derived from degraded date pits. The invention relates further to a method of treatment using the antibacterial peptide.

In some embodiments the animal will already have an infection and the antibacterial peptide or the degraded date pit composition is administered to treat the bacterial infection or reduce the bacterial load. In other embodiments the animal may not have an infection e.g. the antibacterial peptide or the degraded date pit composition is administered to prevent or delay the onset of a bacterial infection in the animal.

The term "degraded date pit" refers to a composition wherein date pits have been treated such that dietary fibres in the date pits are broken down into their digestible units.

One method for obtaining degraded date pit comprises treating date pits with a fungus to obtain a degraded date pit composition. A fungus suitable for degrading date pits is *Trichoderma reesei*. Other fungus, such as yeast, and which are capable of breaking down indigestible fibres found in date pits into digestible units can also be used. *Trichoderma reesei* can degrade date pits by breaking down mannan fibre into different products such as free mannose and mannan-oligosaccharides (MOS). Other fibres that *Trichoderma reesei* can break down into their digestible units include lignin, cellulose and hemicelluloses.

Figure 1:
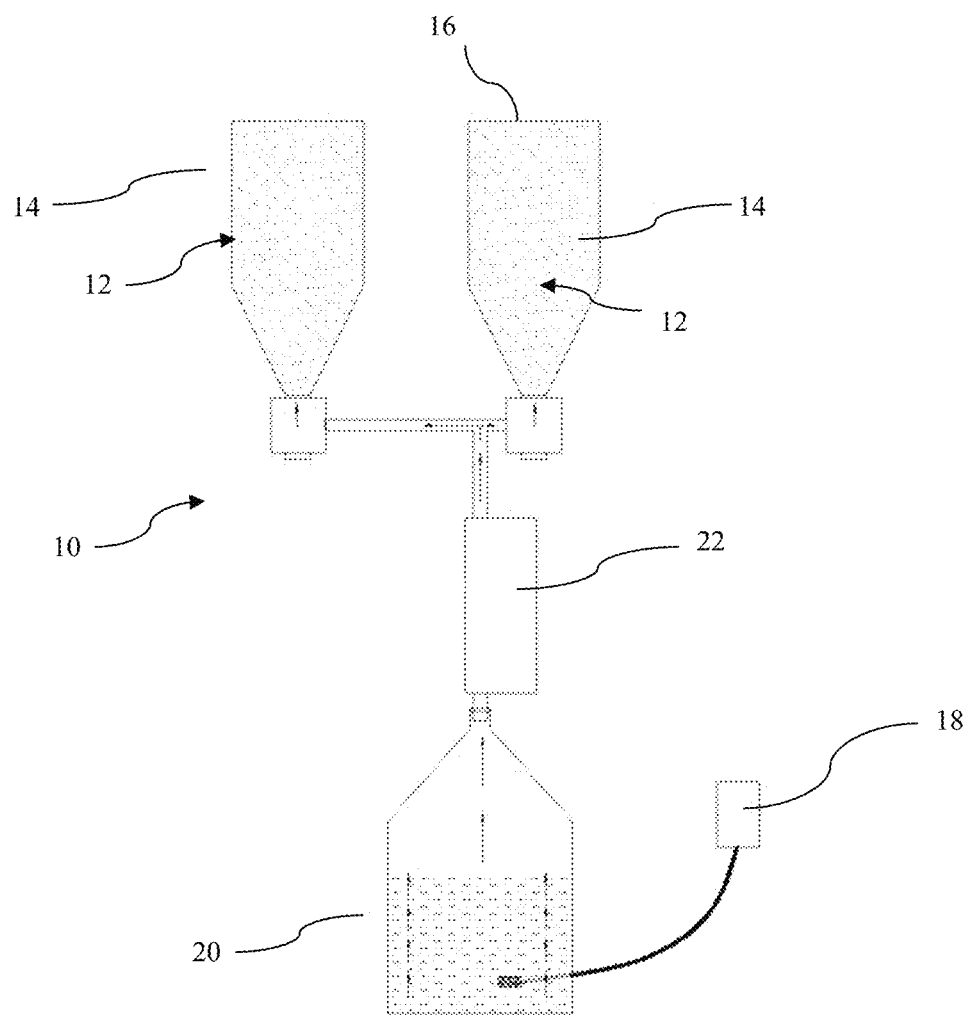
FIG. 1 shows a schematic view of a Solid State Degradation system.

The date pits can be treated within a solid state degradation system by incubating the fresh dates in the presence of *Trichoderma reesei* under conditions suitable to promote degradation of the date pits. A solid state degradation system 10 as exemplified in FIG. 1 can be used to process the date pits. The date pits and fungi 12 are layered within a series of cones 14. Each cone 14 is closed by a cover 16, to avoid contamination. Preferably the cover is a fibre glass cover. During incubation air is blown from an air supply 18 into a water tank 20. The moist air created is then supplied to the cones 14. A disinfection unit 22 treats the moist air before it is supplied to the cones.

Once a degraded date pit composition is obtained it can be mixed with conventional animal feed ingredients to produce a supplemented animal feed composition having antibacterial properties.

The term "feed composition", refers to a preparation providing nutritional value to the animal. Preferred animals are treated by administering an affective amount of the antibacterial peptide. These animals include but are not limited to, cattle, pigs, goats, sheep, fish, horses, and poultry such as chickens, turkey, ducks, geese, ostriches, quails, pheasants or other domestic fowl. Preferably the animal being treated is poultry. An effective amount refers to an amount of the antibacterial peptide which is effective, upon single or multiple dose administration to a subject, in treating or preventing a bacterial infection beyond that than would have been expected in the absence of such a treatment.

Any conventional animal feed composition may be supplemented with the degraded date pit composition. An animal feed can comprise a blend of corn, soybean meal, limestone, salt, dicalcium phosphate, vitamins, minerals, amino acids (such as DL-methionine and lysine), corn oil, fish meal. The feed composition can comprise further components such as further amino acids, enzymes and other nutritional components. The feed composition can be prepared by mixing the ingredients together in the required portions. The feed composition can comprise different portions of ingredients depending on the age of the animal the composition is being fed to. Thereby, having different feed compositions administered at different stages of the animal's life.

The degraded date pits can be added to the feed composition during the manufacture of the feed composition. The degraded date pits can be mixed with the conventional ingredients used in animal feeds or the degraded date pits can replace all or a portion of the conventional animal feed. For example a portion of the corn or soy component can be replaced with an equivalent amount of degraded date pits.

Alternatively the degraded date pit composition may be an additive added to a pre-formulated feed composition prior to feeding of the feed composition to the animal.

The degraded date pit composition can be in the form of a powder.

The degraded date pit composition is present in the feed at a concentration, or administered in an effective amount which provides an antibacterial effect in the animal. An effective amount refers to an amount of the degraded date pit composition which is effective, upon single or multiple dose administration to a subject, in treating or preventing a bacterial infection beyond that than would have been expected in the absence of such a treatment.

The term "antibacterial effect" refers to the ability of the antibacterial peptide or the degraded date pit composition to preventing or delaying the onset of a bacterial infection in animal, to reducing the microbial load in animals and/or to inhibit the growth or kill bacterium in the animals. Exemplary bacterial pathogens include *Escherichia coli*, *Shigella* spp., *Salmonella* spp., *Camplyobacter* spp, *Pseudomonas* spp, and a *Staphylococcus* spp.

The degraded date pit composition or the antibacterial peptide can be present in the feed at a concentration which provides an equivalent antibacterial effect as that achieved by the use of conventional antibiotic supplemented feed, such as a feed supplemented with oxytetracycline.

The present invention is illustrated by the following example and is provided for exemplification purposes only. The particular examples, materials, amounts, and procedures are not intended to limit the scope of the invention.

Example 1

Preparation of Fungus Culture

*Trichoderma reesei* is grown on potato dextrose agar (PDA) at 25+2° C. for 7 days in the dark.

To confirm that the fungi could degrade the date pits a ground date pits based inoculum was prepared by adding half a kilogram of ground date pits and 150 ml of distilled water into 1 liter flasks. The flasks were autoclaved at 121° C. for 30 min on 3 consecutive days. Under aseptic conditions the ground date pits were then inoculated with 8 agar plugs (6 mm diameter) from actively growing margins of the *Trichoderma reesei* colony. The flasks were incubated at 25+2° C. in the dark for three weeks. The flasks were shaken occasionally to ensure uniform colonisation of the date pits by the fungi. Colonized ground date pits which had been autoclaved twice served as a control.

Small amounts of the colonised and control ground date pits were plated onto PDA to confirm that *T. Reesei* was present or absent, respectively.

Preparation of Fungi-Degraded Date Pits

Fungi-degraded date pits were produced using a Solid State Degradation (SSD) system inside an incubator.

Date pits of *Phoenix dactylifera* dates were crushed and grounded using a medium size mill (Skiold Saeby9300, Denmark) to reduce the size of the pits to about 1 mm in diameter. The ground date pit substrate was mixed, cleaned and sterilized three times at 121° C. for 30 minutes.

Sterilized date pit substrate was added to each cone of the SSD system. The starter culture of the fungus, *Trichoderma reesei*, prepared on PDA as described above, was added to each cone of the SSD system containing some of the sterilized date pit substrate. Further fungi cultures and sterilized date pits were added in layers until the volume of fungi and date pits reached 8 litres per cone. The cones are covered in order to avoid any contamination.

A continuous supply of moistened air is supplied to the SSD system. An Aquafine Ultra violet disinfection system provided the fungi and date pits with disinfected moist air during the incubation period. The SSD system is kept within a darkened room at a relative humidity of 90% and a temperature of 30° C. over a 3 week period.

At the end of the 3 week period the process was stopped and the degraded date pits with the fungi mass was collected and transferred to a refrigerator and kept at 4° C. until use in the feed.

Preparation of Poultry Feed

Six isocaloric-isonitrogenous diets were prepared. The diets were prepared as described in Table 1 (starter diet) and Table 2 (finisher diet).

All feed ingredients were ground to a suitable size and mixed in a commercial mixer for 20 minutes. Vitamin and mineral premixes, fish meal and oil were gradually added with continuous mixing the wet mix was then pass through a commercial mixer for 15 minutes for a homogenous distribution of the nutrients and particle sizes. The feed containing the degraded date pits were stored until use at 4° C.

For those feed containing the degraded and non-degraded date pits, the date pit additive was added to the feed alongside the vitamin and mineral premixes. The degraded date pits were prepared as described above.

Prevention of Pathogenic Infections

To illustrate the effect of degraded date pit based feed on pathogenic infections in poultry two hundred, day old chickens were divided into six groups. Each chicken was housed in separate cleaned and sanitized Petersime brooding battery cages and kept in a well cleaned and disinfected poultry house. Water and feed were provided on an ad libitum basis.

Each group was fed with a different feed composition as follows:
1. Group 1 (control)—corn soy diet
2. Group 2 (control)—corn soy diet+antibiotic added (oxytetracycline 20%, 50 g/100 kg)
3. Group 3—5% non-degraded date pits corn-soy diet
4. Group 4—10% non-degraded date pits corn-soy diet
5. Group 5—5% degraded date pits corn-soy diet
6. Group 6—10% degraded date pits corn-soy diet The trial was divided into two periods. Period one (the starter period) started from day 1 to day 21. Period two (the finisher period) started from date 22 to day 33.

During the starter period the chickens were feed a diet having the following composition:

TABLE 1

| Ingredient Name | Control (kg) | 5% non-degraded date pits (kg) | 10% non-degraded date pits (kg) | 5% degraded date pits (kg) | 10% degraded date pits (kg) |
|---|---|---|---|---|---|
| Yellow corn | 59.4 | 53.7 | 46.6 | 53.7 | 46.6 |
| Soybean meal | 32 | 30.76 | 31.25 | 30.76 | 31.25 |
| Salt | 0.4 | 0.38 | 0.38 | 0.38 | 0.38 |
| Limestone | 1.1 | 1.05 | 1.1 | 1.05 | 1.1 |
| Dicalcium phosphate | 1.56 | 1.22 | 1.2 | 1.22 | 1.2 |
| Vitamin and Mineral Premix | 1 | 1 | 1 | 1 | 1 |
| DL-Methionine | 0.24 | 0.24 | 0.25 | 0.24 | 0.25 |
| Lysine | — | 0.1 | 0.1 | 0.1 | 0.1 |
| Corn oil | 2 | 3.35 | 5.02 | 3.35 | 5.02 |
| Fish meal | 2.3 | 3.2 | 3.1 | 3.2 | 3.1 |
| Non-Degraded Date pits | — | 5 | 10 | — | — |
| Degraded Date pits | — | — | — | 5 | 10 |

During the finisher period the chickens were feed a diet having the following composition:

TABLE 2

| Ingredient Name | Control (kg) | 5% non-degraded date pits (kg) | 10% non-degraded date pits (kg) | 5% degraded date pits (kg) | 10% degraded date pits (kg) |
|---|---|---|---|---|---|
| Yellow corn | 64.6 | 58.25 | 52.14 | 58.25 | 52.14 |
| Soybean meal | 28.4 | 27.72 | 26 | 27.72 | 26 |
| Salt | 0.42 | 0.36 | 0.33 | 0.36 | 0.33 |
| Limestone | 1.33 | 1.22 | 1.15 | 1.22 | 1.15 |
| Dicalcium phosphate | 1.05 | 0.95 | 0.8 | 0.95 | 0.8 |
| Vitamin and Mineral Premix | 0.2 | 0.2 | 0.2 | 0.2 | 0.2 |
| DL-Methionine | 0.2 | 0.2 | 0.3 | 0.2 | 0.3 |
| Lysine | 0.1 | 0.1 | 0.18 | 0.1 | 0.18 |
| Corn oil | 2.5 | 4.05 | 5.9 | 4.05 | 5.9 |
| Fish meal | 1.2 | 1.95 | 3 | 1.95 | 3 |
| Non-Degraded Date pits | — | 5 | 10 | — | — |
| Degraded Date pits | — | — | — | 5 | 10 |

At the end of the trial period microbial population densities in dry chicken gut tissue were determined for: total bacterial counts, *Salmonella* spp., *Campylobacter* spp., *Shigella* spp. and *Escherichia coli*.

Microbial population densities in log 10 colony-forming units/g dry chicken gut were determined by the serial dilution tenfold plate assay. The results are shown in Table 3.

TABLE 3

| Treatments | Population density (mean log$_{10}$ cfu per g dry gut tissue) | | | | |
|---|---|---|---|---|---|
| | Total bacterial counts | Salmonella spp. | Campylobacter spp. | Shigella spp. | Escherichia coli |
| (1) Control (without antibiotics) | 8.53 ± (0.88)$^a$ | 2.03 ± (0.13)$^a$ | 2.74 ± (0.09)$^a$ | 2.12 ± (0.07)$^e$ | 7.19 ± (0.14)$^a$ |
| (2) Control With antibiotics | 4.21 ± (0.14)$^b$ | 0.03 ± (0.03)$^b$ | 0.08 ± (0.05)$^b$ | 0.53 ± (0.06)$^b$ | 2.06 ± (0.18)$^b$ |
| (3) With 5% un-degraded date pits | 7.07 ± (0.91)$^c$ | 1.41 ± (0.08)$^c$ | 2.01 ± (0.10)$^c$ | 1.90 ± (0.07)$^{de}$ | 5.53 ± (0.14)$^c$ |
| (4) With 10% un-degraded date pits | 6.02 ± (0.12)$^d$ | 1.48 ± (0.11)$^c$ | 0.95 ± (0.07)$^d$ | 1.67 ± (0.09)$^d$ | 4.61 ± (0.16)$^d$ |
| (5) With 5% degraded date pits | 4.99 ± (0.11)$^e$ | 0.61 ± (0.10)$^d$ | 0.10 ± (0.06)$^b$ | 0.78 ± (0.11)$^c$ | 3.06 ± (0.17)$^e$ |
| (6) With 10% degraded date pits | 3.95 ± (0.12)$^b$ | 0.05 ± (0.05)$^b$ | 0.06 ± (0.04)$^b$ | 0.25 ± (0.09)$^a$ | 2.21 ± (0.13)$^b$ |

The values in Table 3 are means of 6 replicates for each treatment and the values in parentheses are the standard error of the mean. Values with the same letter within a column are not significantly (P>0.01) different according to Fisher's Protected LSD Test.

Chicken gut samples from Group 1 (control group without antibiotics added) had significantly higher (P<0.01) higher total microbial populations than the chicken gut samples fed degraded and un-degraded date pits treatments (group 3, 4, 5, and 6) as well as the control diet with added tetracyclin antibiotic (group 2).

The estimated total populations of total aerobic bacteria, Escherichia coli, Salmonella spp., Shigella spp. and Camplyobacter spp. are significantly (P<0.01) lower in the samples with degraded and un-degraded date pits (groups 3, 4, 5, and 6) compared to the sample without date pits (group 1). There are also significant (P<0.01) decreases in microbial populations by increasing the concentration of date pits.

The treatment which included degraded date pits in 10% concentration (group 6) is significantly superior to other treatments in suppressing microbial population and is shown to provide a reduction in microbial loads equivalent to that achieved by the use of an antibiotic supplemented feed (group 2).

These results show that the degraded date pits could replace conventional antibiotics such as, oxytetracycline-20% in the treatment and prevention of bacterial infections in poultry.

During the trial weight gain and feed intake where measured. The feed conversion ratio (FCR), was calculated. The feed conversion ratio is defined as the amount of feed (in kg) consumed by the animal to produce 1 kg of weight gain. The averaged results per chicken are shown in Table 4.

TABLE 4

| Treatments | Weight-Gain Starter (g) (WGS) | Weight-Gain Total (g) (WGT) | Feed-Intake Starter (g) (FIS) | Feed-Intake Total (g) (FIT) | Feed-Conversion Ratio Starter (FCRS) | Feed-Conversion Ratio Total (FCRT) |
|---|---|---|---|---|---|---|
| (1) Control (without antibiotics) | 866 | 1694.0 | 1200.6 | 1437.0 | 1.387 | 1.557 |
| (2) Control (with antibiotics) | 829.7 | 1729.3 | 1167.5 | 1282.9 | 1.420 | 1.423 |
| (3) With 5% non-degraded date pits | 923.3 | 1778.7 | 1250.1 | 1488.6 | 1.353 | 1.540 |
| (4) With 10% non-degraded date pits | 900.3 | 1729.7 | 1250.9 | 1439.4 | 1.387 | 1.556 |
| (5) With 5% degraded date pits | 835.7 | 1619 | 1199.8 | 1340.5 | 1.450 | 1.570 |
| (6) With 10% degraded date pits | 840 | 1652.7 | 1214.6 | 1387.2 | 1.450 | 1.573 |

The total weight gain from groups 5 and 6 (degraded date pits) were not significantly difference (P>0.05) from the group 2 (control group with antibiotics added). There was no significant difference on body weight gain in the poultry when degraded date pits were added to the feed composition to treat and prevent bacterial infections.

These results show that the treatment and prevention of bacterial infections in poultry can be achieved by replacing part of a conventional feed composition with degraded date pits, as an alternative to using conventional antibiotics, whilst still achieving substantially the same weight gains and FCR as achieved when conventional antibiotics are administered.

Further changes can be made within the scope of the invention. For example other processes can be used to obtain a degraded date pit composition. The degraded date pit compositions can be added to poultry feeds having a different composition. The degraded date pit compositions can be administered to other animals.

Example 2

Methods

A batch of 100 kg of the Khals variety of date pits was obtained from Al Foah date factory, PO Box 18454, Al Ain, United Arab Emirates.

The date pits were divided into three separate sub batches, namely: sub batch 1, sub batch 2 and sub batch 3.

Sub batch 1 comprises non-degraded date pits which act as a control batch. The non-degraded control (sub batch 1) was not treated with the fungus *Trichoderma reesei* and was used for comparison purposes, as will become clear from the paragraphs below. Samples or aliquots were taken from the non-degraded control (sub batch 1) for the purpose of chemical analysis, electron microscopy evaluation and bacteriological studies, respectively, as will be set out more fully below.

Sub batch 2 comprises degraded date pits degraded by a wet degradation method described in Belal IEH, "Evaluation fungi-degraded date pits as a feed ingredient for Nile tilapia *Oreochromis niloticus* L", Aquaculture Nutrition, 2008, vol. 14, pages 445-452, hereinafter referred to as the "wet degradation method" and "Belal 2008". The wet degradation sub batch (sub batch 2) was processed precisely in accordance with the procedure for wet degradation of the date pits disclosed in Belal 2008, thereby to produce a processed wet degradation sub batch which is equivalent to the degraded date pit composition disclosed in Belal 2008. At the end of the degradation (10 days) sub samples or aliquots were taken from the processed wet degradation sub batch (sub batch 2) for the purpose of chemical analysis and bacteriological studies, respectively, as will be explained in detail herein below.

Sub batch 3 comprises degraded date pits degraded by the solid state degradation method as described hereinabove under Example 1. At the end of the degradation period (21 days) samples or aliquots were taken from the processed solid state degradation sub batch (sub batch 3) for the purpose of chemical analysis and bacteriological studies, as will be explained in detail below.

The aliquots from each of sub batch 1, sub batch 2 and sub batch 3 were chemically analyzed in the Animal Nutrition Lab, United Arab Emirates University, Al Ain using high performance liquid chromatography and gas chromatography. The results of the analysis are set out in FIGS. 2 to 8 and are discussed in more detail herein below.

Aliquots from each of sub batch 1, sub batch 2 and sub batch 3 were sent for biological analysis and were tested for their antibacterial and/or antibiotic properties in the Microbiology Laboratory, Department of Biology, College of Science, United Arab Emirates University. The results of the analysis are shown in FIGS. 9 to 15 and 18 are set out and discussed in more detail herein below.

Results of Chemical Analysis

The results of the chemical analysis are set out in the tables shown in FIGS. 2 to 8.

More specifically, the tables in FIGS. 2 to 8 show the results of the analysis of the aliquots taken from the non-degraded sub batch (sub batch 1), the processed wet degradation sub batch (sub batch 2) and the processed solid state degradation sub batch (sub batch 3), respectively.

Referring to FIGS. 2 to 8, it can be clearly seen that the processed wet degradation sub batch (sub batch 2) is significantly different from the processed solid state degradation sub batch (bath 3).

More specifically, referring to FIGS. 2 and 3, from a comparison of the percentages of components found in the processed wet degradation sub batch (sub batch 2) and the processed solid state degradation sub batch (sub batch 3), it is clear that there are differences in respect of each and every component analyzed, with the exception of Fructose which was not found in either sample.

It can also be seen from FIG. 2 that, whereas the mannan oligosaccharide content in the processed solid state degradation sub batch (sub batch 3) is 30.7%, it is only 18.2% in the processed wet degradation sub batch (sub batch 2) and only 17.3% in the non-degraded sub batch (sub batch 1).

Accordingly, the processed solid state degradation sub batch (sub batch 3) contains significantly more mannan oligosaccharide than does both the non-degraded sub batch (sub batch 1) and the processed wet degradation sub batch (sub batch 2).

It can further be seen from FIG. 3 that, whereas the mannose content in the processed solid state degradation sub batch (sub batch 3) is 23.5%, it is only 8.1% in the processed wet degradation sub batch (sub batch 2) and only 7.2% in the non-degraded sub batch (sub batch 1).

Accordingly, the processed solid state degradation sub batch (sub batch 3) contains significantly more mannose than does both the non-degraded sub batch (sub batch 1) and the processed wet degradation sub batch (sub batch 2). More specifically, the processed solid state degradation sub batch (sub batch 3) contains more than double the amount of mannose compared to the amount of mannose found in the non-degraded sub batch (sub batch 1) and the processed wet degradation sub batch (sub batch 2).

Referring to FIGS. 4 to 8, it can also be clearly seen that the processed wet degradation sub batch (sub batch 2) is significantly different from the processed solid state degradation sub batch (sub batch 3) from the comparisons provided in FIGS. 4 to 8 which will not be discussed further for the sake of brevity.

Conclusions from Chemical Analysis

The results of the chemical analysis clearly demonstrate that the fungi-degraded date pit composition prepared by solid state degradation (sub batch 3) is significantly different from the fungi-degraded date pits composition described in Belal 2008 (sub batch 2).

The fact that the processed solid state degradation sub batch (sub batch 3) contains significantly more mannan oligosaccharide than does both the non-degraded sub batch (sub batch 1) and the processed wet degradation sub batch (sub batch 2), clearly demonstrates the surprising and unexpected advantage which the fungi-degraded date pit composition prepared through solid state degradation possesses over the composition of Belal 2008 and over un-degraded date pits.

Furthermore, the fact that the processed solid state degradation sub batch (sub batch 3) contains more than double the amount of mannose compared to the amount of mannose found in the non-degraded sub batch (sub batch 1) and the processed wet degradation sub batch (sub batch 2), clearly demonstrates the surprising and unexpected advantage which the fungi-degraded date pit composition prepared through solid state degradation possesses over the composition of Belal 2008 and over un-degraded date pits.

Methods Used in Bacteriological Studies

The aliquots from each of sub batch 1, 2 and 3 were soaked in sterilized deionized water for 45 minutes, filtered through normal filter paper, and then filtered through sterilized Millipore bacteriological filters (0.22 µm in diameter) to remove any fungal cells/and or spores from the crude extracts.

After filtration with bacteriological filters, the crude extracts from the aliquots taken from the three sub batches were tested against different Gram-positive and Gram-negative bacteria.

The bacteria used were the Gram-positive bacterium *Staphylococcus aureus* and the Gram-negative bacteria *Pseudomonas aeruginosa, Salmonella typhimurium*, and *Escherichia coli*. These type strains bacteria were cultivated in nutrient broth medium and incubated at 37° C. for 48 hours until the concentration of every bacteria reached $1 \times 10^7$ colony forming units ml-1.

Sterilized nutrient agar medium was prepared, sterilized in the autoclave, cooled to 50° C., seeded individually with 20 ml of every bacterium grown in nutrient broth medium and the medium were poured into sterilized Petri dishes in the laminar air flow cabinet.

After solidification of the agar plates, a hole was made in the middle for each Petri dish using sterilized cork borer.

Aliquots (0.6 ml) of the crude extract from each sub batch were added to the hole of a different one of each of the Petri dishes. All plates were incubated in the incubator at 37° C. for 48 hours. The width of inhibition zones around the hole were measured in mm after 48 hours of incubation.

Results of Biological Studies

FIG. 9 shows the effect of adding the crude extract of the degraded date pits prepared with the wet degradation method (sub batch 2) or the degraded date pits prepared with the solid state degradation method (sub batch 3) on the growth of different Gram-positive and Gram-negative bacteria. The diameter of inhibition zones were measured in mm after 48 hours of incubation at 37° C. Un-degraded date pits (sub batch 1) was used as a control treatment.

Figure 10:
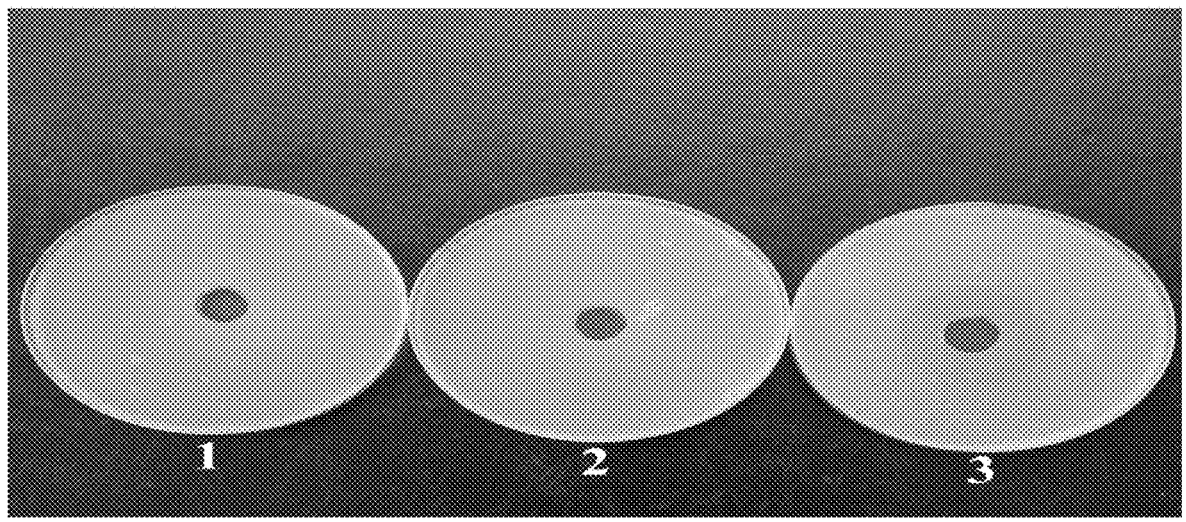
FIG. 10 shows the antibacterial effect of wet degraded date pits, solid state degraded date pits and non-degraded date pit on *Escherichia coli*.

FIG. 10 shows the effect of adding the crude extract of the degraded date pits prepared with the wet degradation method (sub batch 2) or the degraded date pits prepared with the solid state degradation method (sub batch 3) on the growth of *Escherichia coli*. Diameter of inhibition zones were measured in mm after 48 hours of incubation at 37° C. Un-degraded date pits were used as a control treatment (sub batch 1).

Figure 11:
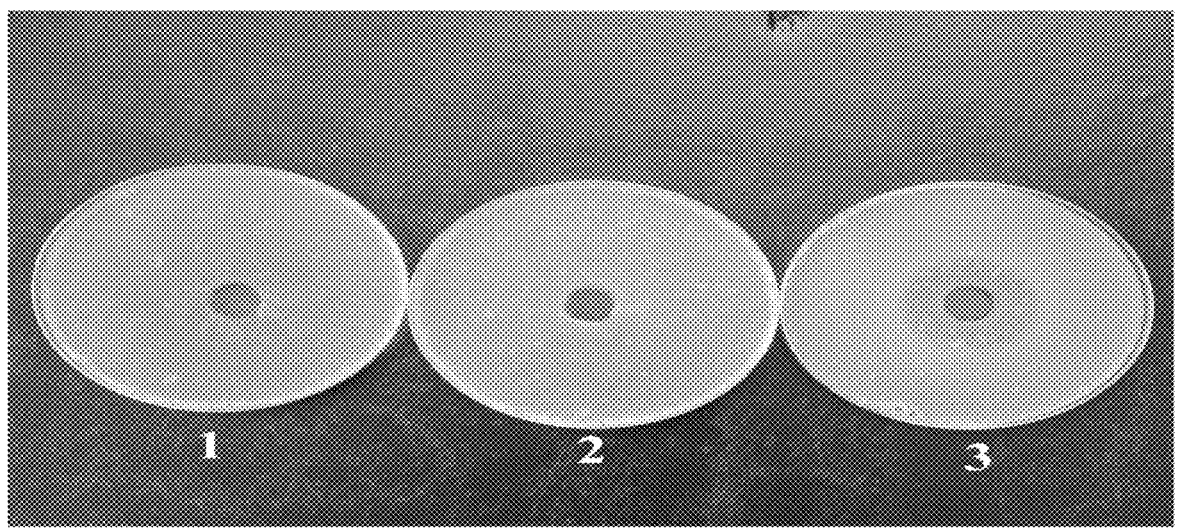
FIG. 11 shows the antibacterial effect of wet degraded date pits, solid state degraded date pits and non-degraded date pit on *Pseudomonas aeruginosa*.

FIG. 11 shows the effect of adding the crude extract of the degraded date pits prepared with the wet degradation method (sub batch 2) or the degraded date pits prepared with the solid state degradation method (sub batch 3) on the growth of *Pseudomonas aeruginosa*. Diameter of inhibition zones were measured in mm after 48 hours of incubation at 37° C. Un-degraded date pits were used as a control treatment (sub batch 1).

Figure 12:
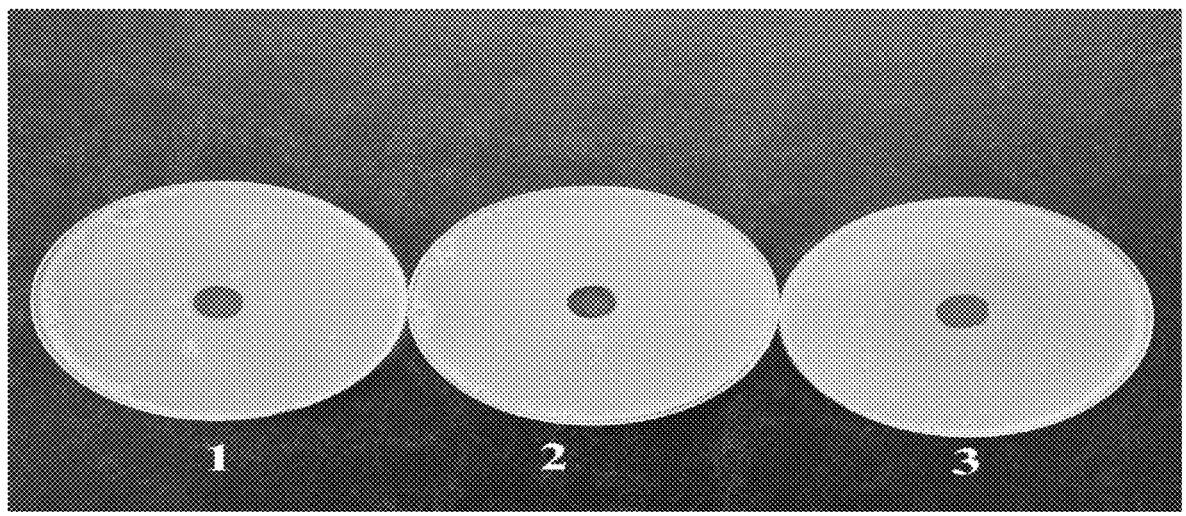
FIG. 12 shows the antibacterial effect of wet degraded date pits, solid state degraded date pits and non-degraded date pit on *Salmonella typhimurium*.

FIG. 12 shows the effect of adding the crude extract of the degraded date pits prepared with the wet degradation method (sub batch 2) or the degraded date pits prepared with the solid state degradation method (3) on the growth of *Salmonella typhimurium*. Diameter of inhibition zones were measured in mm after 48 hours of incubation at 37° C. Un-degraded date pits were used as a control treatment (sub batch 1).

Figure 13:
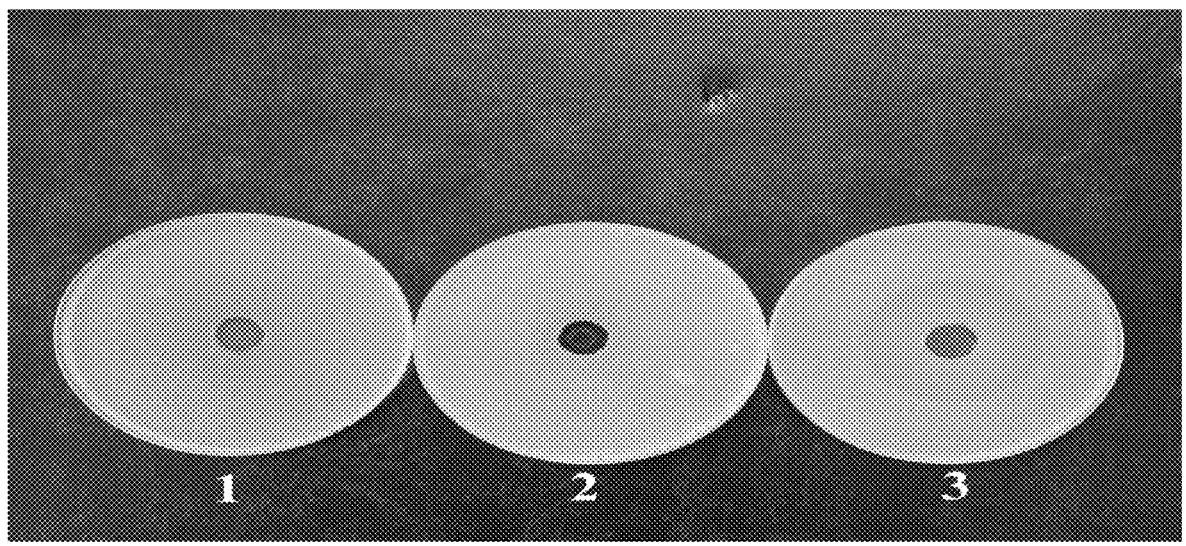
FIG. 13 shows the antibacterial effect of wet degraded date pits, solid state degraded date pits and non-degraded date pit on *Staphylococcus aureus*.

FIG. 13 shows the effect of adding the crude extract of the degraded date pits prepared with the wet degradation method (sub batch 2) or the degraded date pits prepared with the solid state degradation method (sub batch 3) on the growth of *Staphylococcus aureus*. Diameter of inhibition zones were measured in mm after 48 hours of incubation at 37° C. Un-degraded date pits were used as a control treatment (sub batch 1).

The crude extract of the degraded date pits using the wet degradation method of Belal (2008) (sub batch 2) did not show any antibacterial metabolites or antibacterial activities when it was tested against different Gram-positive and Gram-negative bacteria.

The crude extract of the degraded date pits using the wet degradation method of Belal (2008) (sub batch 2) showed similar results when compared to the control experiment in which un-degraded date pits (sub batch 1) was used.

However, the crude extract of the degraded date pits using the solid state degradation method (sub batch 3) showed antibacterial metabolites active against different Gram-positive and Gram-negative bacteria as showed in FIG. 9 and in FIGS. 10, 11, 12 and 13.

From these results it is clear that there is a significant difference between the antibacterial metabolites produced by the degraded date pits produced by the solid state degradation method (sub batch 3) compared to the degraded date pits produced by the wet degradation method of Belal 2008 (sub batch 2) which showed no antibacterial activities as showed in FIG. 9 and in FIGS. 10, 11, 12 and 13.

In FIG. 9, each value is a mean of four replicates. Values with the same letter within a row are not significantly (P>0.05) different according to Fishers protected LSD test.

As can be seen from FIGS. 10 to 13, the crude extract of the degraded date pits using the wet degradation method of Belal (2008) (sub batch 2) did not show any antibacterial metabolites or antibacterial activities when it was tested against different Gram-positive and Gram-negative bacteria.

As can be seen from FIGS. 10 to 13, the crude extract of the degraded date pits using the solid state degradation method (sub batch 3) showed significant antibacterial metabolites active against different Gram-positive and Gram-negative bacteria.

Conclusions from Biological Studies

The results of the biological analysis also clearly demonstrate that the fungi-degraded date pit composition prepared by solid state degradation (sub batch 3) is significantly different from the fungi-degraded date pits composition described in Belal 2008 (sub batch 2).

More specifically, it is clear from a comparison of the results shown in FIG. 9 and from FIGS. 10 to 13, that there are distinct differences in antibacterial properties of sub batch 1, sub batch 2 and sub batch 3, as can be seen from a comparison of the results shown in FIG. 9 and from FIGS. 10 to 13.

The fact that the processed solid state degradation sub batch (sub batch 3) has significant antibacterial qualities when compared to both the non-degraded sub batch (sub batch 1) and the processed wet degradation sub batch (sub batch 2), clearly demonstrates the surprising and unexpected advantage which the fungi-degraded date pit composition prepared through solid state degradation possesses over the composition of Belal 2008 and over un-degraded date pits.

Example 3

Analysis of Peptides Obtained from Sub Batch 1, Sub Batch 2 and Sub Batch 3

Three samples were collected from sub batch 1, sub batch 2 and sub batch 3, respectively. More specifically, sample 1 (non-degraded date pits sample) was collected from sub batch 1, sample 2 (Belal 2008 sample) was collected from sub batch 2 and sample 3 (solid state degradation sample) was collected from sub batch 3.
Extraction of Peptides Peptides were isolated from sample 1, sample 2 and sample 3 and were characterised by the method of Siow and Gan, 2013 (Hwee-Leng Siow, Chee-Yuen Gan 2013). Extraction of antioxidative and antihypertensive bioactive peptides from *Parkia speciosa* seeds. Food Chemistry 141: 3435-3442).

In respect of each of sample 1, sample 2 and sample 3, degraded date pits powder obtained from grinding the samples, was treated with phosphate buffer (10 millilitre, pH 8.0) and different substrate-to-enzyme ratio of alcalase enzyme (20 and 50). The suspension was then incubated at 25° C. and 50° C. with constant shaking at 200 rpm for different time intervals (30 min, 1 hour, 2 hour, and 5 hour). The sample was then heated in a boiling water bath for thirty minutes to end the hydrolysis step, and centrifuged (10000× g, thirty minutes, 4° C.). For further analysis, the collected fraction was stored at −80° C.
Analysis of Peptides by Sodium Dodecyl Sulphate Polyacrylamide Gel Electrophoresis (SDS PAGE)

In respect of each of sample 1, sample 2 and sample 3 peptides were analysed by SDS-PAGE based on the method of Shapiro et al., 1967 (Shapiro A. L., Viñuela E., Maizel J. V. J. 1967. "Molecular weight estimation of polypeptide chains by electrophoresis in SDS-polyacrylamide gels." Biochem Biophys Res Commun. 28 (5): 815-820) and Laemmli, 1970 (Laemmli UK. 1970. Cleavage of structural proteins during the assembly of the head bacteriophage T4. Nature. 227: 680-685).

Resolving gel (15%) and stacking gel (4%) were used for the electrophoretic analysis of peptides. Sample buffer and 2-mercaptoethanol were used for adding samples into the well. After an incubation of 95° C. for five minutes, samples were loaded into the well. Gel running was carried out at 7 mA constant current and resolving at 80-100 V constant voltage. Electrophoretic separation was monitored by the movement of tracking dye bromophenol blue. Gel was placed in staining solution for 1 hr and destained until a clear gel with distinct bands was obtained. For comparison, standard protein marker (Molecular weight 4.0-210.4 kDa) was used.
Fractionation of Peptides In respect of each of sample 1, sample 2 and sample 3, centrifugal ultrafiltration filters were used for fractionation of peptides. Membranes of molecular weight cut-off of 10, 30 and 50 kDa were used. The sample was centrifuged at 4,500×g for fifteen minutes through a filter of 50 kDa. The retentate was collected as a fraction >50 kDa and washed 3 times via centrifugation using the same filter and deionised distilled water. The filtrate obtained was then centrifuged at 10000×g for fifteen minutes and passed through a 30 kDa membrane. The resulting filtrate was a fraction of 30-50 kDa. The filtrate was filtered with a 10 kDa membrane, centrifuged at 4500×g for fifteen minutes, washed 3 times and the resulting filtrate was a fraction <10 kDa.
Antibacterial Activity of Each Fraction Checked Each fraction obtained from sample 1, sample 2 and sample 3 were checked for antibacterial activity using the invitro disc diffusion method of Murray et al; 1995 (Murray P R, Baron E J, Pfaller M A, Tenover F C, Yolke R H. (1995). Manual of Clinical Microbiology, ASM, Washington, D.C. 6th edition), and Bauer et al, 1966 (Bauer A W, Kirby W M, Sherris J C, Turk M. (1966). Antibiotic susceptibility by a standardized single disk method. Am J Clin Pathol; 45:493-6). In an inoculated agar plate, one hundred microlitre of bacteria solution was spread. 20 μL of peptide fractions of various concentrations were inserted into empty sterilized discs. The reference standard used for the study was Ampicillin (10 μg/disc). Incubation of the inoculated plates was overnight at thirty-seven degrees Centigrade. Antibacterial effect was evaluated by analysing the inhibition zone in millimeters against the bacteria tested.

The fractions were compared to an Ampicillin standard of 10 μg/mL.
Amino Acid Profile Amino acid profile was analysed in respect of each of sample 1, sample 2 and sample 3, by the method of El-Adawy et al., 2001 (El-Adawy T. A., Rahma E. H., El-Bedawey A. A., Gafar A. F. 2001. Nutritional potential and functional properties of sweet and bitter lupin seed protein isolates, Food Chemistry 74, 455-462).
Antibacterial Activity of Each Amino Acid Sequence Checked Each amino acid sequence identified in each of samples 1, sample 2 and sample 3, were checked for antibacterial activity using the invitro disc diffusion method of Murray P R et al; 1995 (Murray P R, Baron E J, Pfaller M A, Tenover F C, Yolke R H. (1995). Manual of Clinical Microbiology, ASM, Washington, D.C. 6th edition.)

The amino acid sequences were also compared to an Ampicillin standard of 10 μg/mL
Identification of Fractionated Peptides by Reverse Phase Liquid Chromatography The fractionated peptide fractions in respect of each of sample 1, sample 2 and sample 3 were identified by the method of Gerber et al., 2004 (Gerber, F., Krummen, M., Potgeter, H., Roth, A., Siffrin, C., Spoendlin, C. 2004. "Practical aspects of fast reversed-phase high-performance liquid chromatography using 3 μm particle packed columns and monolithic columns in pharmaceutical development and production working under current good manufacturing practice." Journal of Chromatography A. 1036 (2): 127-133) and Peng Guo et al, 2015 (Peng Guo, Yijun Qi, Chuanhe Zhu, Qun Wang. 2015. Purification and identification of antioxidant peptides from Chinese cherry (*Prunus pseudocerasus* Lindl.) seeds. Journal of Functional Foods 19:394-403).

Fractionated peptides were purified by RPHPLC by the method of Gerber et al., 2004 & Peng Guo et al., 2015. A $C_{18}$ semi preparation column (250 mm×4.6 id) was used for HPLC. A linear gradient of acetonitrile/water (5-100% in 60 min, containing 0.1% TFA) was used for elution at a flow rate of one millilitre per minute and obtained peaks were measured at 220 nm. An automated fraction collector was used for collecting the active fractions of eluted peak and positive fractions were concentrated and stored at −20° C. These eluted fractions were sequenced, as explained in more detail hereinbelow.

Results of Analysis of Peptides in Sub Batch 1, Sub Batch 2 and Sub Batch 3

The results of the analysis of peptides in sub batch 1, sub batch 2 and sub batch 3 are shown in FIG. 14 to 18.

FIG. 14 shows a table showing anti-bacterial activity of peptide fractions from non-degraded date pits. FIG. 15 shows a table showing anti-bacterial activity of <10 kDa, 10-30 kDa, 30-50 kDa and >50 kDa peptide fractions from date pits degraded by wet degradation and date pits degraded by solid state degradation. FIG. 16 shows a table showing the peptide sequences present in date pits degraded by wet degradation. FIG. 17 shows a table showing the peptide sequences present in date pits degraded by solid state degradation. FIG. 18 shows a table showing the antibacterial activity of indentified antibacterial sequences (SEQ ID NO:4 and SEQ ID NO:6) from the peptide sequences shown in FIG. 17.

CONCLUSIONS

As can be seen from FIG. 14, the peptides fractioned from sample 1 showed no antibacterial activity.

FIG. 15 shows that in sample 2 (date pits degraded by a wet degradation method) only one fraction (>50 kDa) has minimal antibacterial properties against one bacterial species, namely, *Bacillus subtilis*.

FIG. 15 also shows that in sample 3 (date pits degraded by the solid state degradation) all fractions had antibacterial activities. Furthermore, the <10 kDa showed maximum antibacterial activity. FIG. 15 further shows that sample 3 (date pits degraded by the solid state degradation) showed maximum antibacterial activity against four bacterial species, namely, *E. coli, Salmonella typhimurium, Staphylococcus aureus, Bacillus subtilis*.

From FIGS. 16 and 18 it can be seen that the >50 kDa fractions of sample 2 have 11 sequences. Among them only one sequence has minimum antibacterial activity.

From FIGS. 17 and 18 it can be seen that in sample 3 (date pits degraded by the solid state degradation) the <10 kDa fraction have several sequences among them two sequences showed maximum anti-bacterial activity, namely SEQ ID NO: 4 and SEQ ID NO:6.

SEQ ID NO: 4 is Lys-Arg-Gly-Arg-Leu-Ile-Trp-Arg-Val-Trp-Arg-Gly-Ile-Trp.

SEQ ID NO:6 is Arg-Gln-Trp-Ile-Ser-Arg-Trp-Thr-Trp-Gln-Arg.

Without wanting to be bound by the theory, the Applicant believes that SEQ ID NO: 4 and SEQ ID NO:6 are effective as antibacterial agents as the sequences contain maximum number of aromatic and basic amino acids like tryptophan, arginine and lysine. The presence of specific amino acids at specific position in the peptide chain is important for the expression of antimicrobial activity. This depends on functional groups of amino acids.

Without wanting to be bound by the theory, the Applicant also believes that in the in SEQ ID NO: 4 and SEQ ID NO:6 of sample 3, the amino acids tryptophan and arginine are present in repeating units and the positive charge and hydrophobic group of these two amino acids promotes the anti-bacterial activity. Without wanting to be bound by the theory, the Applicant also believes that the cationic nature and hydrogen bonding property of arginine and tryptophan helps to bind each other and to destroy the bacterial cells, thereby increasing the antimicrobial property of peptides. The Applicant also believes that other amino acids like glutamine, isoleucine and serine are also present in the sequence of sample 3 that accelerates the antibacterial activity.

From FIG. 18 it can also be seen that the antibacterial activity of the sample 3 peptides SEQ ID NO: 4 and SEQ ID NO:6 are comparable to the standard drug ampicillin.

The Applicant has advantageously found that the antibacterial activity of the sample 3 peptides SEQ ID NO: 4 and SEQ ID NO:6 provide a new product antibacterial product that can be derived from date pits which are readily available in a number of countries and which have typically been seen as waste product from the preparation of dates and are usually discarded.

The Applicant envisages that the sample 3 peptides SEQ ID NO:4 and SEQ ID NO:6 are advantageous because they may be isolated from date pits degraded by solid state degradation, as explained and described hereinabove.

The Applicant further envisages that the sample 3 peptides SEQ ID NO:4 and SEQ ID NO:6 are advantageous because they represent natural peptides which are antibacterial in nature against both Gram-positive and Gram-negative bacteria while at the same time are biocompatible and non-toxic to cells.

The Applicant also envisages that the sample 3 peptides SEQ ID NO:4 and SEQ ID NO:6 are suitable to be used in animal feed and are more advantageous than antibiotics, as the sample 3 peptides SEQ ID NO:4 and SEQ ID NO:6 will not accumulate in the animal body when used in animal feed, but will rather metabolized and/or degraded in the animal body into amino acids and eliminated via the urea cycle. As such, the sample 3 peptides, especially, SEQ ID NO:4 and SEQ ID NO:6, are advantageous over antibiotics because residual antibiotics in the animal body is not desirable for human consumption.

The Applicant also envisages that the sample 3 peptides, especially, SEQ ID NO:4 and SEQ ID NO:6, are suitable to be used in animal feed as both an antibacterial agent and as a growth promoter.

The Applicant also envisages that the sample 3 peptides, especially SEQ ID NO:4 and SEQ ID NO:6, may be isolated from the date pits degraded by the solid state degradation as described hereinabove.

Alternatively, the Applicant envisages that the sample 3 peptides SEQ ID NO:4 and SEQ ID NO:6 may be produced synthetically, as its sequence has been determined as explained hereinabove. As such, the invention extends to a synthetic amino acid sequence including the amino acid sequence of SEQ ID NO:4 or SEQ ID NO:6.

The invention claimed is:

1. A method of treating an infection in an animal caused by one or more of a *Salmonella* species, a *Bacillus* species, an *Escherichia* species, a *Pseudomonas* species, and a *Staphylococcus* species, the method comprising: administering to the animal an effective amount of a peptide having the amino acid sequence comprising one or more of:

(a) SEQ ID NO:4
(b) SEQ ID NO:6.

2. The method as claimed in claim 1, wherein the peptide has the amino acid sequence comprising SEQ ID NO:4.

3. The method as claimed in claim 1, wherein the peptide has the amino acid sequence comprising SEQ ID NO:6.

\* \* \* \* \*